United States Patent
Torisawa et al.

(10) Patent No.: US 8,945,000 B2
(45) Date of Patent: Feb. 3, 2015

(54) DISTAL END HOOD FOR ENDOSCOPE AND ENDOSCOPE SYSTEM

(75) Inventors: Nobuyuki Torisawa, Kanagawa (JP); Koji Yoshida, Kanagawa (JP); Hiroshi Shibuya, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 66 days.

(21) Appl. No.: 13/288,808

(22) Filed: Nov. 3, 2011

(65) Prior Publication Data

US 2012/0116165 A1  May 10, 2012

(30) Foreign Application Priority Data

Nov. 5, 2010  (JP) .................................. 2010-248893

(51) Int. Cl.
- A61B 1/04 (2006.01)
- A61B 1/273 (2006.01)
- A61B 1/015 (2006.01)
- A61B 1/00 (2006.01)
- A61B 1/12 (2006.01)

(52) U.S. Cl.
CPC ............ *A61B 1/2736* (2013.01); *A61B 1/00089* (2013.01); *A61B 1/00101* (2013.01); *A61B 1/015* (2013.01); *A61B 1/00119* (2013.01); *A61B 1/126* (2013.01)
USPC ......................................... 600/127; 600/129

(58) Field of Classification Search
USPC ......... 600/127, 129, 104, 114, 121–123, 153, 600/157; 348/45; 356/241.1
See application file for complete search history.

(56) References Cited

U.S. PATENT DOCUMENTS

| | | | | |
|---|---|---|---|---|
| 4,735,501 | A | * | 4/1988 | Ginsburgh et al. ......... 356/241.1 |
| 5,386,817 | A | * | 2/1995 | Jones ............................ 600/104 |
| 5,630,795 | A | * | 5/1997 | Kuramoto et al. .............. 604/30 |
| 2005/0090709 | A1 | * | 4/2005 | Okada et al. .................. 600/104 |
| 2005/0222491 | A1 | | 10/2005 | Noda et al. |
| 2006/0241348 | A1 | | 10/2006 | Kohno |

(Continued)

FOREIGN PATENT DOCUMENTS

| | | |
|---|---|---|
| EP | 1 707 107 A1 | 10/2006 |
| JP | 57-120004 | 7/1982 |

(Continued)

OTHER PUBLICATIONS

Notification of Reason(s) for Rejection dated Oct. 25, 2012, with English translation.

(Continued)

*Primary Examiner* — Alireza Nia
*Assistant Examiner* — Timothy J Neal
(74) *Attorney, Agent, or Firm* — McGinn IP Law Group, PLLC

(57) ABSTRACT

A distal end hood for an endoscope configured to be mounted on a distal end portion of an endoscope including an observation window, and a distal end surface of the distal end portion on which an opening is formed, the opening configured to spray a feed gas, the distal end hood for an endoscope including a conduit including: a first end portion on which a first opening is formed, the first opening being fitted together by insertion with an opening of the distal end surface of the distal end portion of the endoscope and being connectable to the opening; and a second end portion on which a second opening is formed, the second opening being disposed at a position away from the distal end surface toward a proximal end side of the endoscope.

10 Claims, 9 Drawing Sheets

(56) References Cited

U.S. PATENT DOCUMENTS

| | | |
|---|---|---|
| 2007/0163585 A1 | 7/2007 | Uesugi et al. |
| 2007/0255165 A1 | 11/2007 | Uesugi et al. |
| 2009/0048486 A1* | 2/2009 | Surti .............................. 600/127 |
| 2009/0198212 A1* | 8/2009 | Timberlake et al. .......... 604/506 |

FOREIGN PATENT DOCUMENTS

| | | | |
|---|---|---|---|
| JP | 01229220 A * | 9/1989 | ............. G02B 23/24 |
| JP | 2-139602 | 11/1990 | |
| JP | 7-313443 A | 12/1995 | |
| JP | 2005-287839 A | 10/2005 | |
| JP | 2006-280535 A | 10/2006 | |
| JP | 2006-325816 A | 12/2006 | |
| JP | 2009-131467 A | 6/2009 | |
| WO | WO 2007/080971 A1 | 7/2007 | |

OTHER PUBLICATIONS

Notification of Reasons for Rejection dated May 31, 2013 with English translation.
Extended European Search report dated Aug. 21, 2013.
European Office Action dated Jun. 18, 2014.

* cited by examiner

FIG.3A
FIG.3B
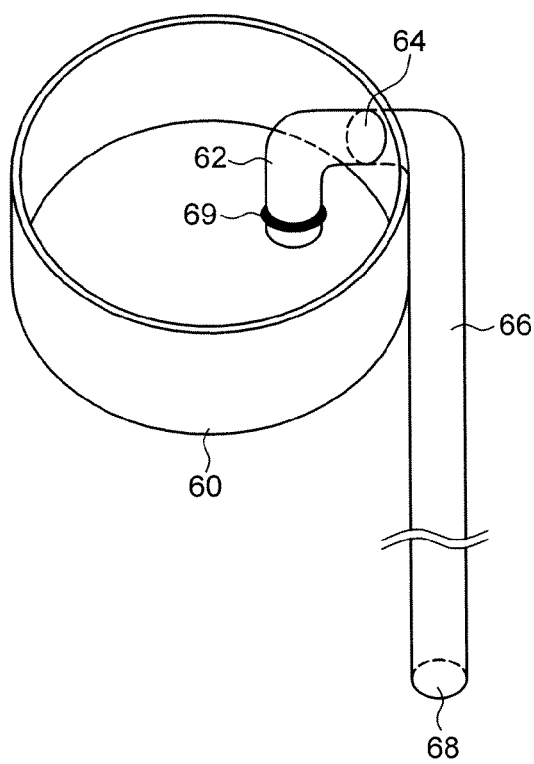
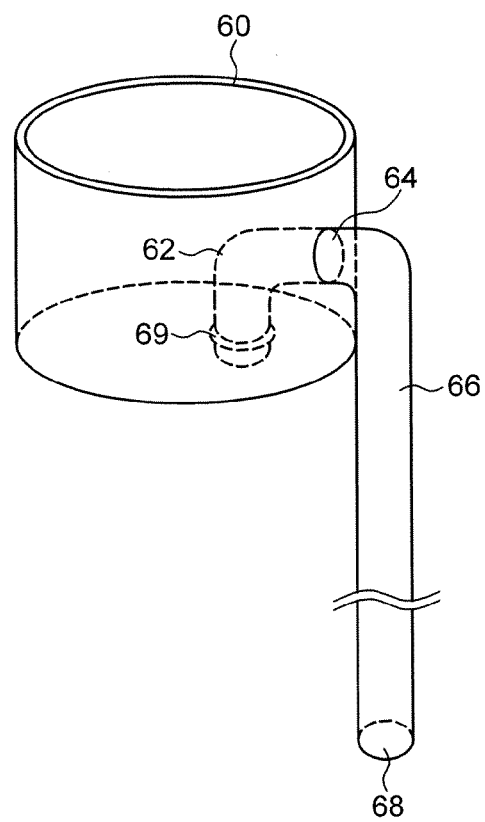

DISTAL END HOOD FOR ENDOSCOPE AND ENDOSCOPE SYSTEM

BACKGROUND OF THE INVENTION

1. Field of the Invention

The presently disclosed subject matter relates to a distal end hood for an endoscope and an endoscope system. More particularly, the presently disclosed subject matter relates to a distal end hood for an endoscope and an endoscope system in which intraluminal observations and treatments are performed by supplying a constant-pressure gas fed from an gas feed unit into a lumen of a subject being tested through an opening provided at a distal end portion of a flexible endoscope inserted into the lumen.

2. Description of the Related Art

Conventionally, medical diagnostics using an endoscope has been widely practiced in the field of medicine. In particular, an image pickup element, such as a CCD (charge-coupled device), is built into a distal end portion of an endoscope to be inserted into a body cavity to take an image of the interior of the body cavity. And, signal processing is performed using a processor unit to display the image on a monitor. Then, a doctor can observe and use this image for diagnosis or inserts a treatment instrument from a treatment instrument insertion channel to perform treatments, such as sample collection and polyp removal.

In laparoscopic surgery in which curative treatments are performed without conducting laparotomy in order to minimize invasion into a patient, a rigid endoscope for observation or a treatment instrument for performing curative treatments is introduced into a body cavity through a plurality of trocars punctured into the abdomen of the patient. At this time, a pneumoperitoneum unit for supplying a pneumoperitoneum gas into an abdominal cavity is used, in order to secure the visual field of the rigid endoscope and an area for operating treatment instruments.

When, for example, an insertion part of a flexible endoscope having flexibility is inserted into a lumen, such as a stomach or a large intestine, to perform intraluminal diagnoses or treatments, a treatment instrument is inserted into a lumen through a forceps channel (treatment instrument channel) of the flexible endoscope to perform curative treatments therein. Also, at this time, a constant-pressure feed gas, such as a carbon dioxide gas, is supplied into the lumen.

For example, Japanese Patent Application Laid-Open No. 2009-131467 describes a system in which a gas is introduced into a gas feed conduit within a pneumoperitoneum unit from a gas cylinder filled with a $CO_2$ gas. In Japanese Patent Application Laid-Open No. 2009-131467, the gas feed conduit is configured so that the $CO_2$ gas is supplied into an abdominal cavity through an pneumoperitoneum tube introduced into the abdominal cavity by way of a gas feeding guide tube (trocar) punctured into the abdominal cavity of a patient.

In addition, Japanese Patent Application Laid-Open No. 2005-287839 describes a system in which a tube for an abdominal cavity and a tube for a lumen are coupled with a gas feed unit, so that a carbon dioxide gas is supplied from the tube for an abdominal cavity into an abdominal cavity through a trocar and that the carbon dioxide gas is supplied from the tube for a lumen into a lumen through a treatment instrument channel.

Yet additionally, Japanese Patent Application Laid-Open No. 2006-280535 describes a system in which a gas is sprayed from a gas/water feed nozzle at a leading end of a gas feed tube to be connected to a gas feed conduit communicated with a cylinder through a coupling member.

SUMMARY OF THE INVENTION

In a constant-pressure gas feed system, however, if a distal end of an endoscope submerges in a liquid or the like accumulated within a body cavity when a gas is sprayed from the endoscope's distal end as in the above-described related art, bubbles are generated since the gas is constantly sprayed from the submerged distal end. Bubbles formed of water mixed with a bodily fluid and the like are less likely to disappear. Then, there is the problem that the bubbles may interrupt the visual field of an observation window formed on a distal end surface of the endoscope.

The presently disclosed subject matter has been accomplished in view of such circumstances as described above. Accordingly, an object of the presently disclosed subject matter is to provide a distal end hood for an endoscope and an endoscope system in which the visual field of an observation window may not be interrupted by bubbles even if the distal end of an endoscope becomes submerged in a liquid, in a constant-pressure gas feed system.

In order to achieve the above-described object, the first aspect of the presently disclosed subject matter provides a distal end hood for an endoscope to be mounted on a distal end portion of an endoscope including an observation window for making observations within the body of a subject being tested and an opening for spraying a constant-pressure feed gas formed on the distal end surface of the distal end portion, wherein the distal end hood for an endoscope includes a conduit one end opening of which is fitted together by insertion with an opening of the distal end surface and is thus connectable thereto and the other end opening of which is disposed at a position away from the distal end surface toward the proximal end side of the endoscope when the distal end hood for an endoscope is mounted on the distal end portion of the endoscope.

Consequently, a constant-pressure feed gas spray port can be disposed away from the distal end surface having the observation window toward the proximal end side of the endoscope. Accordingly, bubbles are prevented from being generated by a sprayed gas and the visual field of the observation window can be secured, even if the distal end portion of the endoscope becomes submerged in a liquid accumulated within a body cavity.

The second aspect of the presently disclosed subject matter provides the distal end hood for an endoscope characterized in that the other end opening of the conduit is positioned at a flexible portion of the endoscope when the distal end hood for an endoscope is mounted on the distal end portion of the endoscope.

By locating the distal end portion of the conduit for spraying a constant-pressure feed gas away from the distal end surface having the observation window, bubbles are prevented from being generated by a sprayed gas and the visual field of the observation window can be secured, even if the distal end portion of the endoscope becomes submerged in a liquid accumulated within a body cavity.

The third aspect of the presently disclosed subject matter provides the distal end hood for an endoscope characterized in that an O-ring for maintaining airtightness when the one end opening of the conduit is fitted together by insertion with an opening of the distal end surface is provided at one end of the conduit.

Consequently, the constant-pressure feed gas can be prevented from leaking at a junction between the opening of the distal end surface and the conduit.

The fourth aspect of the presently disclosed subject matter provides the distal end hood for an endoscope characterized in that the conduit penetrates through a lateral side of the distal end hood for an endoscope.

Consequently, areas near a junction between the conduit and the opening of the distal end surface can be fixed by the distal end hood for an endoscope. And, the observation window can be segregated from the surroundings thereof by the distal end hood for an endoscope to secure the visual field of the observation window.

Also, in order to achieve the above-described object, the fifth aspect of the presently disclosed subject matter provides an endoscope system including: a distal end hood for an endoscope according to any one of the first to fourth aspects; an endoscope including an insertion part to be inserted into an object being examined, a gas feed conduit for supplying a constant-pressure feed gas, and an opening communicated with the gas feed conduit and formed on a distal end surface of the insertion part for spraying the constant-pressure feed gas; and a gas feed unit for supplying the constant-pressure feed gas to the gas feed conduit.

Consequently, a constant-pressure feed gas spray port is located away from the distal end surface having the observation window toward the proximal end side of the endoscope. Accordingly, bubbles are prevented from being generated by a sprayed gas and the visual field of the observation window can be secured, even if the distal end portion of the endoscope becomes submerged in a liquid accumulated within a body cavity, thereby enabling accurate observations and the like to be made.

The sixth aspect of the presently disclosed subject matter provides the endoscope system characterized in that the gas feed conduit for supplying the constant-pressure feed gas is a forceps channel.

The seventh aspect of the presently disclosed subject matter provides the endoscope system characterized in that the gas feed conduit for supplying the constant-pressure feed gas is a gas feed channel formed within the insertion part.

As described above, the conduit for supplying the constant-pressure feed gas is not limited in particular, but the presently disclosed subject matter is applicable to various types of conduits.

As has been described heretofore, according to the presently disclosed subject matter, the constant-pressure feed gas spray port is located away from the distal end surface having the observation window toward the proximal end side of the endoscope. Accordingly, bubbles are prevented from being generated by a sprayed gas and the visual field of the observation window can be secured, even if the distal end portion of the endoscope becomes submerged in a liquid accumulated within a body cavity, thereby enabling accurate observations and the like to be made.

BRIEF DESCRIPTION OF THE DRAWINGS

FIGS. 3A and 3B are perspective views illustrating a distal end hood for an endoscope according to the presently disclosed subject matter, wherein FIG. 3A is a view taken from a position higher than a position from which the view of FIG. 3B is taken;

DETAILED DESCRIPTION OF THE PREFERRED EMBODIMENTS

Hereinafter, a distal end hood for an endoscope and an endoscope system according to the presently disclosed subject matter will be described in detail with reference to the accompanying drawings.

Figure 1:
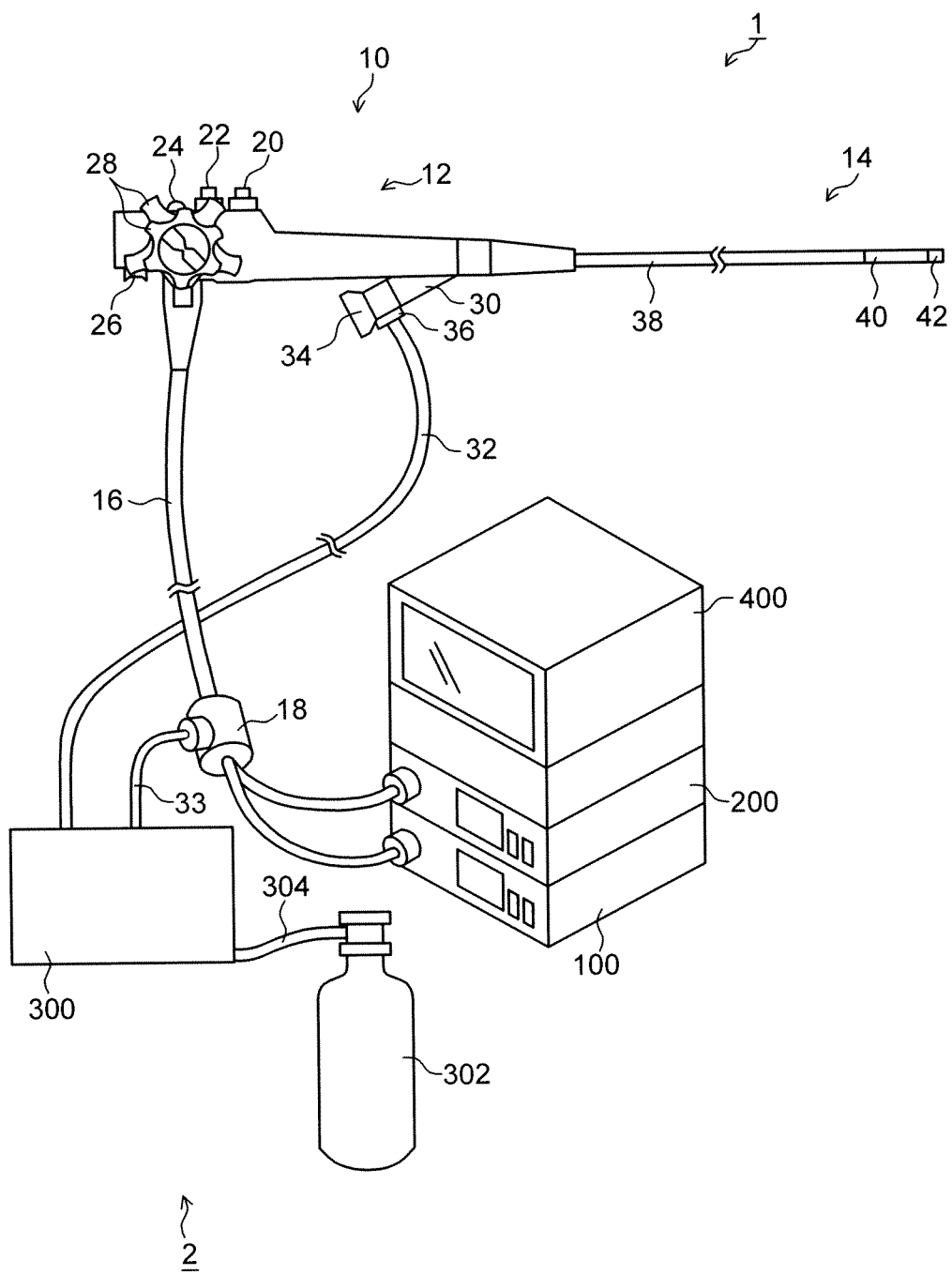
FIG. 1 is an external view illustrating the schematic overall configuration of a first embodiment of an endoscope system according to the presently disclosed subject matter.

FIG. 1 is an external view illustrating the schematic overall configuration of a first embodiment of an endoscope system according to the presently disclosed subject matter.

As illustrated in FIG. 1, an endoscope system 1 is equipped with an endoscope gas feed system 2. The endoscope system 1 includes an endoscope (flexible endoscope) 10, the endoscope gas feed system 2, a light source unit 100, an endoscope processor 200, and a monitor unit 400.

The endoscope 10 includes a hand-operated part 12 and an insertion part 14 connected continuously to this hand-operated part 12. An operator holds the hand-operated part 12 located on the proximal end side of the endoscope to operate the endoscope 10 and, by inserting the distal end side of the insertion part 14 into a lumen of a subject being tested, the operator can perform observations, diagnoses or curative treatments.

A universal cable 16 is connected to the hand-operated part 12, and an endoscope connector 18 is provided on the universal cable 16. By attachably and detachably coupling this endoscope connector 18 with the light source unit 100, illuminating light is sent to an illuminating optical system (not illustrated) disposed at the distal end portion of the insertion part 14. In addition, an electrical connector is connected to the endoscope connector 18 through the universal cable 16, and the electrical connector is attachably and detachably coupled with the endoscope processor 200. Consequently, observation image data obtained with the endoscope 10 is output to the endoscope processor 200, so that an observation image is displayed on the monitor unit 400 connected to the endoscope processor 200.

In addition, the hand-operated part 12 is provided with a gas/water feed button 20, a suction button 22, a shutter button 24, a seesaw switch 26 for zooming operation, angle knobs 28, and a forceps insertion part 30.

The forceps insertion part 30 is communicated with an unillustrated forceps channel formed within the insertion part 14. As will be described later, the forceps channel is communicated with a forceps port (see FIG. 2) of the distal end portion of the endoscope. When a carbon dioxide gas is supplied into a lumen as the constant-pressure feed gas through the forceps channel, an insertion inlet adapter 34 is provided on the forceps insertion part 30. A constant-pressure gas feed tube 32 is coupled with a gas supply cap 36 of the insertion inlet adapter 34. In addition, the other end of the gas feed tube 32 is coupled with a gas feed unit 300.

A carbon dioxide gas cylinder 302 is coupled with the gas feed unit 300 through a high-pressure gas tube 304. A carbon dioxide gas is stored in a liquefied state in the carbon dioxide gas cylinder 302. The carbon dioxide gas stored in the carbon dioxide gas cylinder 302 is introduced from the forceps insertion part 30 to the forceps channel through the gas feed tube 32 by the gas feed unit 300 as a constant-pressure gas regulated to a predetermined pressure, so that the carbon dioxide gas is sprayed into a lumen of a subject being tested from the forceps port of the distal end portion of the endoscope.

In addition, a gas/water feed tube 33 is extended out of the gas feed unit 300 and connected to the endoscope connector 18. The gas/water feed tube 33 is communicated with a gas/water feed channel formed within the insertion part 14 of the endoscope through the conduit of the universal cable 16, so that, as will be described later (see FIG. 2), a gas supplied by the gas feed unit 300 is sprayed from a gas/water feed nozzle formed on the distal end surface toward the observation window.

The insertion part 14 includes a flexible portion 38, a bending portion 40, and a distal end portion 42. The bending portion 40 is remotely bend-operated by rotating a pair of angle knobs 28 provided on the hand-operated part 12. Consequently, the distal end portion 42 can be directed in a desired direction. In addition, the flexible portion 38 connects between the hand-operated part 12 and the bending portion 40, and is made of a flexible member, so as to bend in an optional (random) direction along a direction of insertion into the object being examined.

Figure 2:
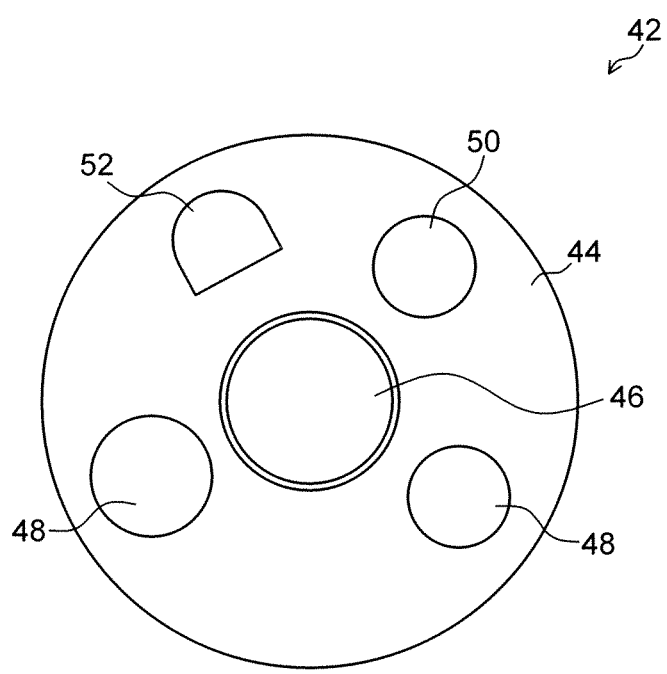
FIG. 2 is a plan view of the distal end surface of a distal end portion of an insertion part.

FIG. 2 illustrates a plan view of a distal end surface 44 of the distal end portion 42 of the insertion part 14.

As illustrated in FIG. 2, an observation window 46, an illumination window 48, a forceps port 50, and a gas/water feed nozzle 52 are disposed on the distal end surface 44 of the distal end portion 42.

An optical system (observation optical system) for capturing image light within an object being examined is disposed at the back of the observation window 46. The captured image light representative of an observation image is received by a CCD and sent to the endoscope processor 200 through a signal cable. The image light is then converted into a video signal at the endoscope processor 200, so that the observation image is displayed on the monitor unit 400 connected to the endoscope processor 200.

Two illumination windows 48 are disposed in symmetrical positions on both sides of the observation window 46, as illustrated in FIG. 2. Illuminating light from the light source unit 100 is irradiated through the illumination windows at an observation site within the object being examined. Light from the light source unit 100 is guided to the illumination windows 48 by an optical fiber (light guide) located within the insertion part 14. Thus, illuminating light is emitted through an illumination lens disposed at a leading end of the optical fiber and a cover glass fitted in each illumination window 48.

The forceps port 50 is connected to a forceps channel (not illustrated) disposed within the insertion part 14 and communicated with the forceps insertion part 30 of the hand-operated part 12. A leading end of each of forceps and various other treatment instruments inserted into the forceps insertion part 30 is exposed out of the forceps port 50 through the forceps channel.

In the present embodiment in particular, a carbon dioxide gas is supplied from the forceps port 50 into a lumen through the forceps channel as the constant-pressure feed gas. When the carbon dioxide gas is supplied into the lumen, the insertion inlet adapter 34 is mounted on the forceps insertion part 30, as described above (see FIG. 1), so that the carbon dioxide gas is supplied into the lumen from the gas supply cap 36 of the insertion inlet adapter 34 through the gas feed tube 32 coupled with the gas feed unit 300.

The gas/water feed nozzle 52 is used to clean the observation window 46 by spraying a cleaning fluid and pressurized air when the observation window 46 becomes contaminated. The gas/water feed nozzle 52 sprays fluids, such as air and cleaning water, toward the observation window 46 in response to gas feed operation and water feed operation performed by using the gas/water feed button 20 provided on the hand-operated part 12. Consequently, bodily fluids and feculence attached to the observation window 46 are cleaned off and thus an excellent visual field is secured.

When a carbon dioxide gas is supplied from the forceps port 50 into a lumen, however, bubbles may be generated due to bodily fluids and water attached to the distal end surface 44. Consequently, the generated bubbles may, for example, cover the observation window 46, thus interrupting the visual field thereof. As a result, the observation window 46 has to be cleaned frequently using the gas/water feed nozzle 52.

Hence, in the present embodiment, one end opening of a long conduit (tube) is connected to the forceps port 50 which is a carbon dioxide gas spray port, this conduit is extended to the proximal end side of the endoscope, and the other end opening of the conduit is located at a position away from the distal end portion 42, thereby spraying a carbon dioxide gas from that position, so that even if bubbles are generated from the carbon dioxide gas sprayed out of the forceps port 50 and from liquids attached to the distal end surface 44, the bubbles do not go into the visual field area of the observation window 46.

In the present embodiment, a hood is mounted on the distal end portion 42 in order to connect this conduit (tube) to the forceps port 50. Thus, the conduit is connected to the forceps port 50 through this hood.

FIGS. 3A and 3B illustrate a distal end hood for an endoscope (hereinafter simply referred to as "hood") according to the presently disclosed subject matter. FIG. 3A is a perspective view taken by looking down at the hood from a significantly elevated position, whereas FIG. 3B is a perspective view taken by looking at the hood from a position lower than the former position.

As illustrated in FIGS. 3A and 3B, a hood 60 is a circular cylinder having a certain thickness, and a thin conduit (tube) 62 bent in an L-shaped manner is disposed inside the hood. The conduit 62 is composed of a portion (horizontal portion) substantially perpendicular to a lateral side of the hood 60 and a portion (vertical portion) bent almost 90 degrees from the horizontal portion and parallel to the axial direction of the hood 60. That is, when the hood 60 is mounted on the distal end portion 42 of the endoscope, the horizontal portion of the conduit 62 is perpendicular to the axial direction of the endoscope, and the vertical portion of the conduit 62 is parallel to the axial direction of the endoscope.

As will be described later, when the hood 60 is mounted on the distal end portion 42 of the endoscope, the distal end opening of the vertical portion of the conduit 62 is fitted together by insertion with the forceps port 50 of the distal end surface 44 and is thus connected thereto.

An edge of a portion of the conduit 62 substantially perpendicular to a lateral side of the hood 60 is connected to an opening 64 formed on the lateral side of the hood 60. In addition, another conduit 66 connected to the opening 64 is provided external to the opening 64. That is, the conduit 62 and the conduit 66 are formed as one conduit communicated with each other, so as to penetrate through the lateral side of the hood 60.

Here, the conduit 66 in particular formed external to the opening 64 is preferably a flexible tube formed of a flexible member, such as rubber. The conduit 66 formed external to the opening 64 as a flexible tube is longer than the length of the hood 60 along the outer lateral side of the hood 60. The conduit 66 is extended in the axial direction thereof, so that a leading end of the conduit 66 reaches the flexible portion 38 when the hood 60 is mounted on the distal end portion 42. A distal end opening 68 for spraying a gas is provided at the distal end portion of the conduit 66. In addition, an edge of the portion of the conduit 62 parallel to the axial direction of the hood 60 extends to a position almost the same as the position of a proximal end side edge of the hood 60. An O-ring 69 is disposed at the leading end of the conduit 62.

Note that the conduit 62 internal to the hood 60 and the conduit 66 external to the hood 60 may be formed as separate members. Alternatively, the conduits 62 and 66 may be formed of a flexible member, such as rubber, as an integral member. For example, a leading end of a tube having a predetermined length may be formed as a portion to serve as the conduit 62, so as to lead the tube from the opening 64 formed on a lateral side of the hood 60 into within the hood 60. Note however that if this tube is too soft, it is difficult to fit the leading end of the tube forming the conduit 62 into the forceps port 50. Accordingly, it is preferable to harden the leading end alone to some degree (it is preferable to make the leading end of the tube harder than the other portion of the tube).

Figure 4:
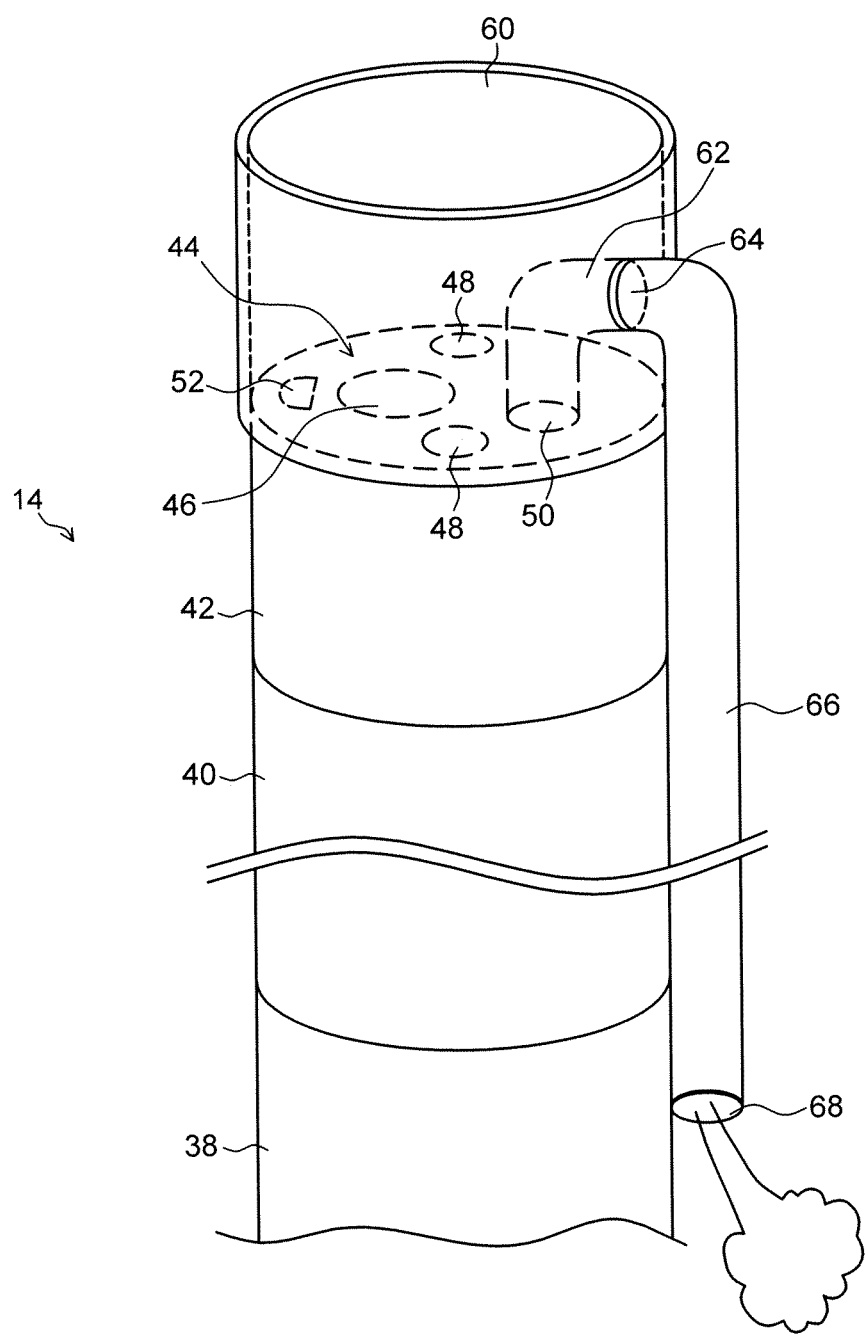
FIG. 4 is a perspective view illustrating a distal end hood for an endoscope mounted on the distal end portion of an endoscope.

FIG. 4 perspectively illustrates the hood 60 mounted on the distal end portion 42 of the endoscope 10.

As illustrated in FIG. 4, the hood 60 is mounted in such a manner that the distal end portion 42 is fitted into the inner circumferential surface of the hood 60. Note that, though not illustrated, a mounting part for the hood 60 to be mounted in a state of being externally fitted onto the outer circumferential surface of the distal end portion 42 is formed on the proximal end side (side for the hood to be mounted on the distal end portion 42) of the hood 60. At this time, a mounting part serving similar to that mounting part of the hood 60 may also be formed in the distal end portion 42. The structure of this mounting part is not limited in particular. Materials of the hood 60 and the conduit 62 are not limited in particular. Materials of the hood 60 may be resin materials, for example. Alternatively, the conduit 62 may be formed of the same material as that of the conduit 66, so as to be integral therewith.

When the hood 60 is fitted and mounted onto the distal end portion 42 of the endoscope 10, one end opening (vertical portion) of the L-shaped conduit 62 is fitted into the forceps port 50 (fitted together therewith by insertion).

At this time, the conduit 62 can be fitted into the forceps port 50 while maintaining airtightness, since the O-ring 69 is provided near an edge of the conduit 62, as illustrated in FIG. 3. Consequently, a carbon dioxide gas is prevented from leaking out of the forceps port 50.

The other edge (horizontal portion) of the conduit 62 one edge (vertical portion) of which is fitted into the forceps port 50 is coupled with the opening 64 on a lateral side of the hood 60. In addition, the conduit 62 is connected to the conduit 66 external to the hood 60 through the opening 64.

As illustrated in FIG. 4, the conduit 66 extends along the axial direction of the insertion part 14, the distal end portion of the conduit 66 reaches the flexible portion 38, and the opening 68 for spraying a gas is provided in the distal end portion of the conduit 66. As described above, one end opening of the conduit 62 is connected to the forceps port 50 which is a constant-pressure feed gas spray port of the distal end surface 44, and the other end opening of the conduit 66 is located far away from the distal end surface 44.

Note that, though not illustrated, the conduit 66 is preferably fixed to a lateral side of the insertion part 14, so that when the hood 60 is mounted on the distal end portion 42, the conduit 66 extending to the flexible portion 38 does not freely move away from the insertion part 14. At this time, the conduit 66, even if fixed to a lateral side of the insertion part 14, can change in shape in conformity to the change in shape of the insertion part 14 since the conduit 66 is formed of a flexible member, such as rubber.

As described above, in the present embodiment, the hood 60 is mounted on the distal end portion 42, the conduit 66 communicated with the forceps port 50 (see FIG. 4) is extended to the proximal end side of the insertion part 14, and the opening 68 is provided in a position away from the distal end portion 42 to spray a gas at that position.

Figure 5:
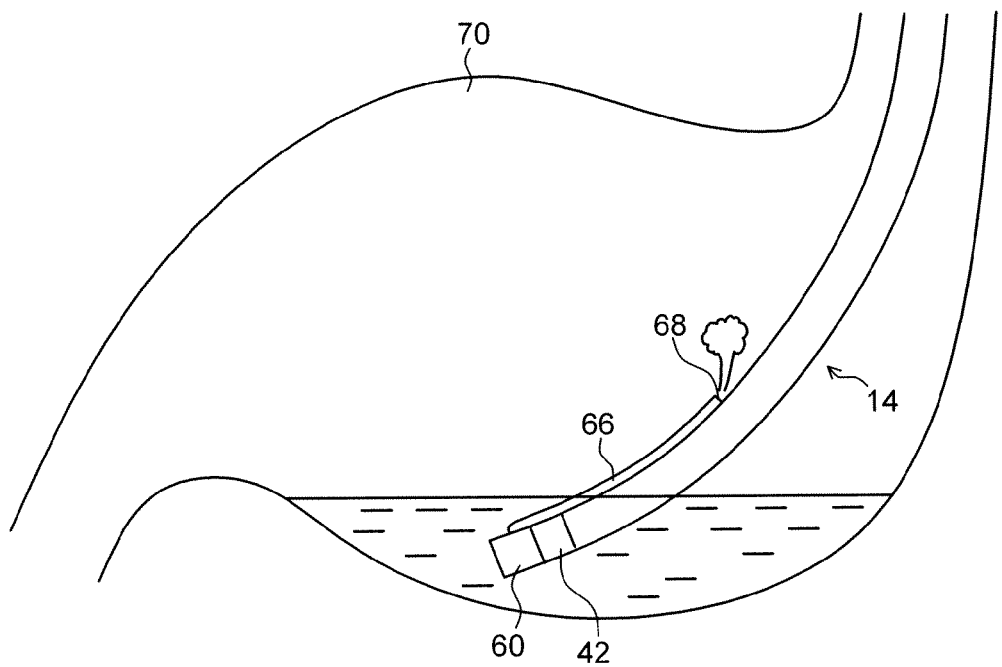
FIG. 5 is an explanatory view illustrating an insertion part of an endoscope inserted into the stomach of a subject being tested.

FIG. 5 illustrates a condition in which the insertion part 14 of the endoscope 10 is inserted into a stomach 70 of a subject being tested. As illustrated in FIG. 5, even if the distal end portion 42 of the insertion part 14 becomes submerged in a liquid accumulated in the stomach 70, the gas spray port does not submerge and bubbles are therefore not generated by the spout of gas.

Accordingly, even in such a case, the visual field of the observation window 46 of the distal end surface 44 can be prevented from being interrupted by bubbles.

Next, a second embodiment of the presently disclosed subject matter will be described.

Figure 6:
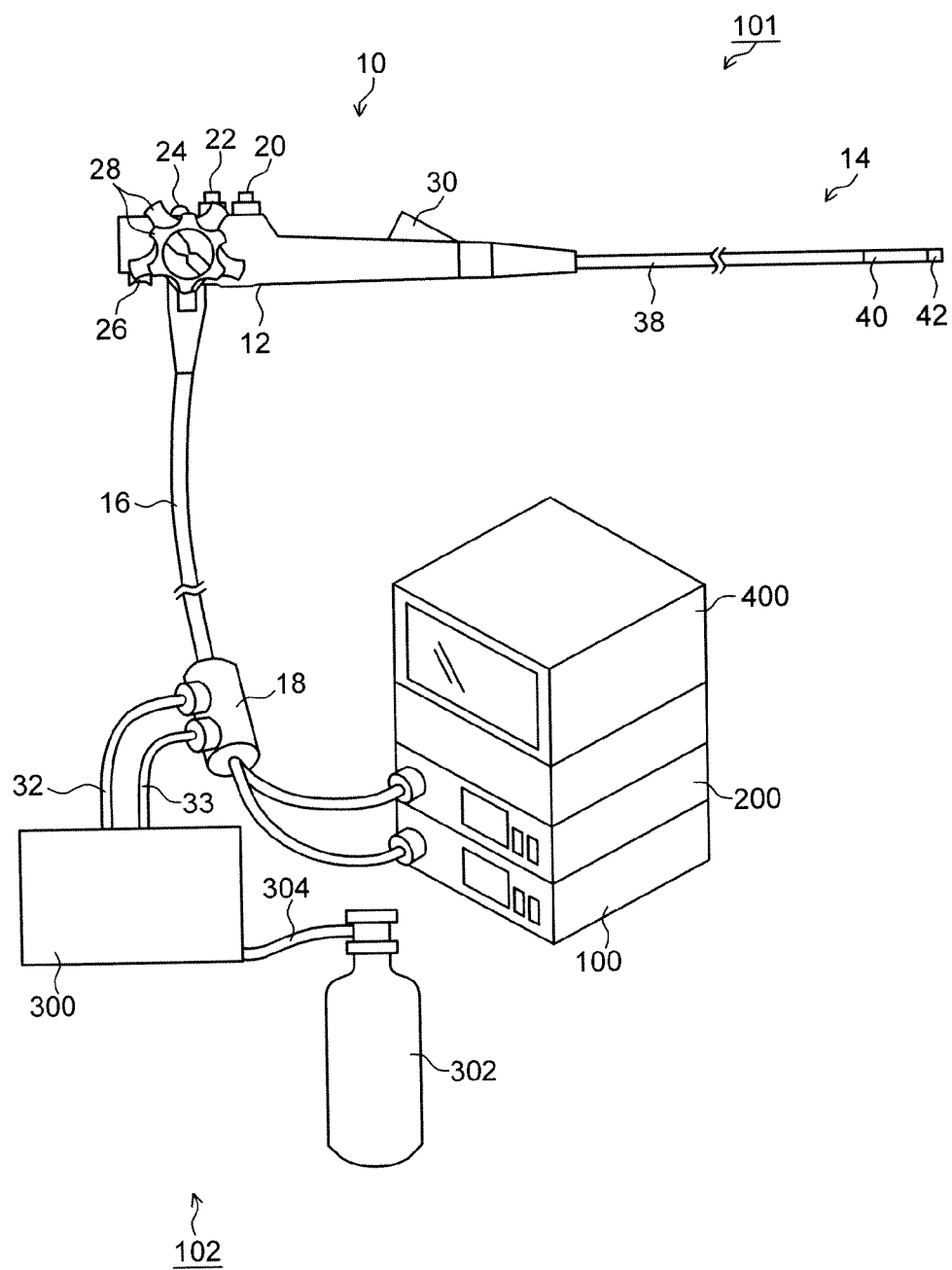
FIG. 6 is an external view illustrating a schematic overall configuration of a second embodiment of an endoscope system according to the presently disclosed subject matter.

FIG. 6 is an external view illustrating a schematic overall configuration of a second embodiment of an endoscope system equipped with an endoscope gas feed system according to the presently disclosed subject matter.

As illustrated in FIG. 6, an endoscope system 101 of the present embodiment is equipped with an endoscope gas feed system 102. The endoscope system 101 also has a configuration substantially the same as that of the endoscope system 1 of the above-described first embodiment. Accordingly, like constituent elements are denoted by the same reference numerals as those of the endoscope system 1 of the first embodiment and will be described in no further detail. The endoscope system 101 includes an endoscope (flexible endoscope) 10, a light source unit 100, an endoscope processor 200 and a monitor unit 400, in addition to the endoscope gas feed system 102.

The endoscope 10 includes a hand-operated part 12 and an insertion part 14. A universal cable 16 is connected to the hand-operated part 12, and an endoscope connector 18 is provided on the universal cable 16. The universal cable 16 is connected to the light source unit 100 and the endoscope processor 200 through the endoscope connector 18.

In the present embodiment, a constant-pressure feed gas is supplied from a constant-pressure feed gas spray port at the leading end of the insertion part 14 through a constant-pressure gas feed channel separately formed within the insertion part 14, rather than from the forceps port 50.

In the first embodiment, the gas feed tube 32 is coupled with the gas supply cap 36 of the insertion inlet adapter 34 provided in the forceps insertion part 30. In the present embodiment, however, one end of the gas feed tube 32 is coupled with the gas feed unit 300 and the other end thereof is communicated from the endoscope connector 18 through the universal cable 16 to the constant-pressure gas feed channel.

A carbon dioxide gas cylinder 302 is coupled with the gas feed unit 300 through a high-pressure gas tube 304. A carbon dioxide gas is stored in a liquefied state in the carbon dioxide gas cylinder 302. The carbon dioxide gas stored in the carbon dioxide gas cylinder 302 is sprayed by the gas feed unit 300, as a constant-pressure gas regulated to a predetermined pressure, out of the spray port of the constant-pressure gas feed channel through the gas feed tube 32 and by way of the endoscope connector 18 through the conduit of the universal cable 16.

In addition, a gas/water feed tube 33 is extended out of the gas feed unit 300 and connected to the endoscope connector 18. The gas/water feed tube 33 is communicated with a gas/water feed channel formed within the insertion part 14 of the endoscope through the conduit of the universal cable 16, so that a gas supplied by the gas feed unit 300 is sprayed from a gas/water feed nozzle formed on the distal end surface 44 toward the observation window.

Figure 7:
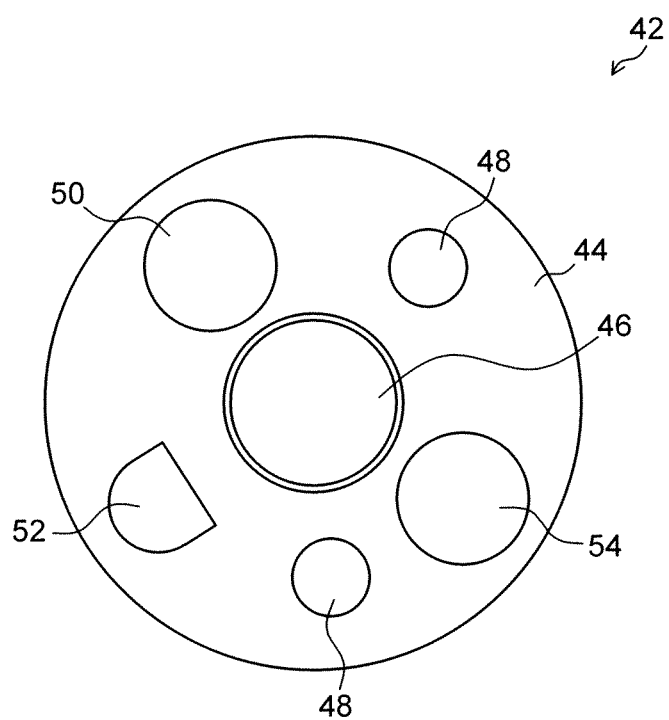
FIG. 7 is a plan view illustrating the distal end surface of a distal end portion of an insertion part of the second embodiment.

FIG. 7 illustrates a distal end surface of the distal end portion 42 of the insertion part 14 of the present embodiment.

As illustrated in FIG. 7, in the present embodiment, a constant-pressure gas feed opening 54 is disposed on the distal end surface 44 of the distal end portion 42, in addition to the observation window 46, the illumination window 48, the forceps port 50, and the gas/water feed nozzle 52.

The constant-pressure gas feed opening 54 forms a distal end opening of an unillustrated constant-pressure gas feed channel formed within the insertion part 14. The constant-pressure gas feed opening 54 is used to spray a constant-pressure feed gas (carbon dioxide gas) supplied from the gas feed unit 300 through the gas feed tube 32, the endoscope connector 18, the conduit of the universal cable 16 and the constant-pressure gas feed channel.

Figure 8:
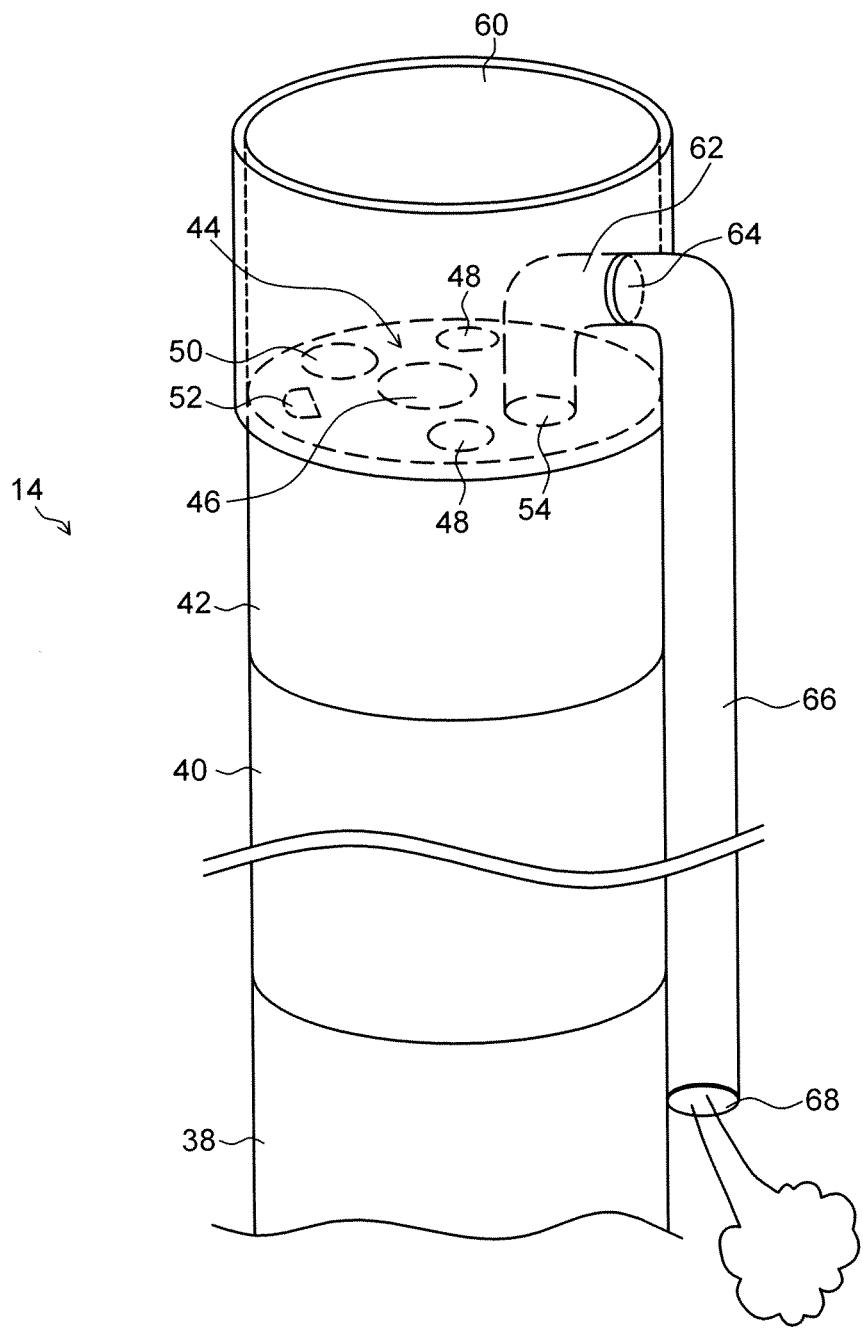
FIG. 8 is a perspective view illustrating a distal end hood for an endoscope mounted on the distal end portion.

FIG. 8 perspectively illustrates the way the hood 60 (see FIG. 3) is mounted on the distal end portion 42.

As illustrated in FIG. 8, the hood 60 is mounted in such a manner that the distal end portion 42 is fitted into the inner circumferential surface of the hood 60. When the hood 60 is mounted on the distal end portion 42, an edge of a portion (vertical portion) of the L-shaped conduit 62 parallel to the axial direction of the hood 60 is just fitted into (fitted together by insertion with) an inner circumferential surface of the constant-pressure gas feed opening 54 formed on the distal end surface 44 of the distal end portion 42. As in the first embodiment, an O-ring for maintaining airtightness is preferably provided in the vertical portion of the conduit 62 to be fitted together by insertion with the inner circumferential surface of the constant-pressure gas feed opening 54.

At this time, an edge of the horizontal portion of the conduit 62 is coupled with an opening 64 on the lateral side of the hood 60. In addition, the conduit 62 is connected to the conduit 66 external to the hood 60 through the opening 64.

The conduit 66 extends along the axial direction of the insertion part 14. The distal end portion of the conduit 66 reaches the flexible portion 38. And, an opening 68 for spraying a gas is provided in the distal end portion of the conduit 66. As in the first embodiment, the conduit 66 is preferably fixed to a lateral side of the insertion part 14, so that when the hood 60 is mounted on the distal end portion 42, the conduit 66 does not move around freely.

As described above, in the present embodiment, the hood 60 is mounted on the distal end portion 42, the conduit 66 communicated with the constant-pressure gas feed opening 54 is extended to the proximal end side of the insertion part 14, and the opening 68 is provided in a position away from the distal end portion 42 to spray a gas at that position.

Consequently, even if the distal end portion 42 of the insertion part 14 becomes submerged in a liquid accumulated within a lumen, the gas spray port does not submerge and bubbles are therefore not generated by the spout of gas.

Note that, as illustrated in FIG. 4 or 8 in the embodiments described above, the conduit 62 and the conduit 66 penetrate through a lateral side of the hood 60 in either case, so as to communicate with each other. However, the conduit 62 and the conduit 66 are not limited to such a configuration.

Figure 9A:
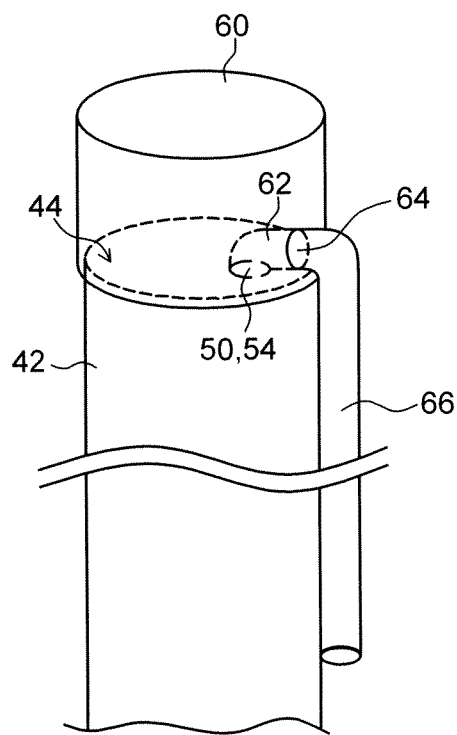
FIGS. 9A and 9B are perspective views illustrating another example of a distal end hood for an endoscope.

For example, as illustrated in FIG. 9A, the conduit 62 connected to the opening (the forceps port 50 or the constant-pressure gas feed opening 54) of the distal end surface 44 may be disposed, so as to crawl along the distal end surface 44, and connected to the conduit 66 through the opening 64 formed on the proximal end side of the hood 60.

Figure 9B:
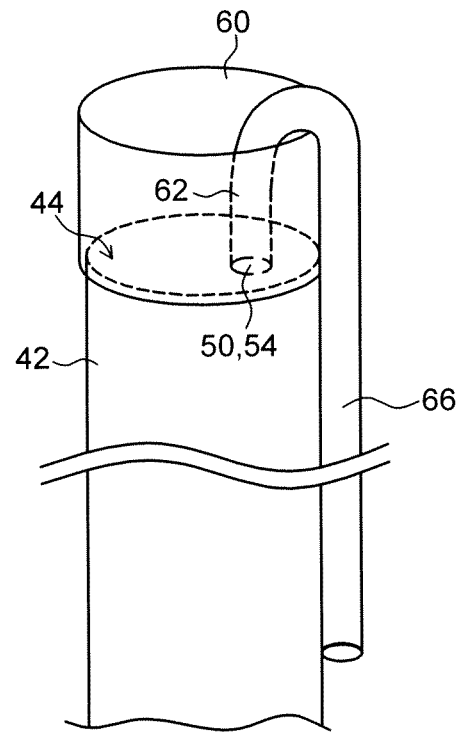

Alternatively, as illustrated in FIG. 9B, the conduit 62 connected to the opening (the forceps port 50 or the constant-pressure gas feed opening 54) of the distal end surface 44 may be formed, so as to extend along the lateral side of the hood 60 to the distal end side thereof and climb over the leading end of the hood 60 to directly connect to the conduit 66.

As has been described heretofore, the presently disclosed subject matter can be suitably applied, no matter whether a constant-pressure feed gas is sprayed out of a forceps port or the constant-pressure feed gas is supplied through a constant-pressure gas feed channel provided separately from the forceps channel and sprayed out of the distal end opening of the constant-pressure gas feed channel. In either case, a constant-pressure gas spray port does not submerge in a liquid even if the distal end portion of an endoscope becomes submerged in the liquid, and therefore, bubbles are not generated.

In addition, a gas feed conduit (lumen) for supplying a constant-pressure feed gas is not limited to such a conduit formed within an insertion part as the above-described forceps channel or gas feed channel. Alternatively, the conduit may be formed independently of the endoscope.

While a distal end hood for an endoscope and an endoscope system according to the presently disclosed subject matter have been described in detail hereinabove, the presently disclosed subject matter is not limited to the above-described embodiments. It is needless to say that various modifications and alterations may be made to the presently disclosed subject matter without departing from the gist thereof.

What is claimed is:

1. A distal end hood for an endoscope, comprising:
a hood portion which is formed in a circular cylindrical shape, the hood portion configured to be mounted on a distal end portion of an insertion part of the endoscope and circularly surround a front side of the distal end portion of the insertion part of the endoscope, the insertion part configured to be inserted into a subject being tested; and
a conduit including a first conduit which is disposed inside the hood portion, and a second conduit which is communicated with the first conduit and is disposed outside the hood portion, the conduit being formed of a flexible tube,
the conduit including:
a first end portion on which a first opening is formed, the first opening being fitted together by insertion with an opening of a distal end surface of the distal end portion of the insertion part and being connectable to the opening, when the distal end hood is mounted on the distal end portion of the insertion part, the opening being configured to spray a feed gas, an observation window being provided on the distal end surface, and
a second end portion on which a second opening is formed, the second opening being disposed at a position away from the distal end surface toward a proximal end side of the insertion part, when the distal end hood is mounted on the distal end portion of the insertion part, wherein the second opening of the conduit is positioned at a flexible portion of the insertion part when the distal end hood is mounted on the distal end portion of the insertion part, the flexible portion being disposed on the proximal end side with respect to a bending portion of the insertion part, the bending portion being disposed on the proximal end side with respect to the distal end portion.

2. The distal end hood according to claim 1, further comprising:

an O-ring configured to maintain airtightness when the first opening of the conduit is fitted together by insertion with the opening of the distal end surface, the O-ring being provided at the first end portion of the conduit.

3. An endoscope system, comprising:
an endoscope; and
a distal end hood for the endoscope,
the endoscope including:
  a distal end portion;
  a bending portion;
  a flexible portion which are disposed in sequential order from a distal end side;
  an insertion part configured to be inserted into a subject being tested;
  a gas feed conduit which is disposed inside the insertion part, the gas feed conduit configured to supply a feed gas;
  a distal end surface of the insertion part on which an opening is formed, the opening configured to be communicated with the gas feed conduit and to spray the feed gas; and
  an observation window which is provided on the distal end surface, the observation window configured to make observations within the body of the subject being tested,
the distal end hood for the endoscope being formed in a circular cylindrical shape, the distal end hood configured to be mounted on the distal end portion of the insertion part of the endoscope and circularly surround a front side of the distal end portion of the insertion part of the endoscope,
the distal end hood including a conduit including a first conduit which is disposed inside the distal end hood, and a second conduit which is communicated with the first conduit and is disposed outside the distal end hood, the conduit being formed of a flexible tube, the conduit further including:
  a first end portion on which a first opening is formed, the first opening being fitted together by insertion with the opening of the distal end surface of the distal end portion of the insertion part and being connectable to the opening, when the distal end hood is mounted on the distal end portion of the insertion part, the opening configured to spray the feed gas; and
  a second end portion on which a second opening is formed, the second opening being disposed at a position away from the distal end surface toward a proximal end side of the insertion part, when the distal end hood is mounted on the distal end portion of the insertion part, wherein the second opening of the conduit is positioned at the flexible portion when the distal end hood is mounted on the distal end portion of the insertion part.

4. The endoscope system according to claim 3, wherein the gas feed conduit comprises a forceps channel.

5. The endoscope system according to claim 3, wherein the gas feed conduit comprises a gas feed channel formed within the insertion part.

6. The endoscope system according to claim 3,
wherein the first conduit comprises a tube including a horizontal portion which is perpendicular to a lateral side of the distal end hood, and a vertical portion which is bent 90 degrees from the horizontal portion and is parallel to an axial direction of the distal end hood,
the horizontal portion is communicated with the second conduit, and
the vertical portion is fitted by insertion with the opening of the distal end surface.

7. The endoscope system according to claim 3, wherein a length of the second conduit is longer than a length of the distal end hood along a lateral side of the distal end hood.

8. The endoscope system according to claim 3, wherein the second conduit is fixed to a lateral side of the distal end hood.

9. The endoscope system according to claim 3, further comprising:
a gas feed unit configured to supply the feed gas to the gas feed conduit.

10. The endoscope system according to claim 3, further comprising:
a light source unit configured to emit illumination light.

* * * * *